(12) United States Patent
Lin et al.

(10) Patent No.: US 10,744,132 B2
(45) Date of Patent: Aug. 18, 2020

(54) SUSTAINED-RELEASE BUPRENORPHINE FORMULATIONS

(71) Applicant: Alar Pharmaceuticals, Inc., Taipei (TW)

(72) Inventors: Tong-Ho Lin, Taipei (TW); Yung-Shun Wen, Taipei (TW); Jui-Wei Liang, Taipei (TW)

(73) Assignee: Alar Pharmaceuticals, Inc., Taipei (TW)

( * ) Notice: Subject to any disclaimer, the term of this patent is extended or adjusted under 35 U.S.C. 154(b) by 0 days.

(21) Appl. No.: 16/098,864

(22) PCT Filed: Sep. 12, 2017

(86) PCT No.: PCT/CN2017/101327
§ 371 (c)(1),
(2) Date: Nov. 4, 2018

(87) PCT Pub. No.: WO2018/050043
PCT Pub. Date: Mar. 22, 2018

(65) Prior Publication Data
US 2019/0142823 A1    May 16, 2019

Related U.S. Application Data

(60) Provisional application No. 62/394,168, filed on Sep. 13, 2016.

(51) Int. Cl.
| | |
|---|---|
| A61K 31/485 | (2006.01) |
| A61K 47/14 | (2017.01) |
| A61K 47/10 | (2017.01) |
| A61K 47/20 | (2006.01) |
| A61K 47/22 | (2006.01) |
| A61K 9/00 | (2006.01) |
| A61P 25/04 | (2006.01) |
| A61P 25/24 | (2006.01) |
| A61P 25/36 | (2006.01) |

(52) U.S. Cl.
CPC ......... *A61K 31/485* (2013.01); *A61K 9/0019* (2013.01); *A61K 47/10* (2013.01); *A61K 47/14* (2013.01); *A61K 47/20* (2013.01); *A61K 47/22* (2013.01); *A61P 25/04* (2018.01); *A61P 25/24* (2018.01); *A61P 25/36* (2018.01)

(58) Field of Classification Search
None
See application file for complete search history.

(56) References Cited

U.S. PATENT DOCUMENTS

2005/0075361 A1*  4/2005  Wang ............... A61K 31/485
514/282

FOREIGN PATENT DOCUMENTS

| CN | 1500786 | * | 6/2004 |
| WO | WO2015/136253 | * | 9/2015 |
| WO | WO 2015/136253 | * | 9/2015 |

OTHER PUBLICATIONS

Meyer et al. in Journal of Pharmaceutical Sciences 96(12) 3155-3167 (2007) (Year: 2007).*

* cited by examiner

*Primary Examiner* — Dennis Heyer
(74) *Attorney, Agent, or Firm* — Amin, Turocy & Watson, LLP

(57) ABSTRACT

An injectable pharmaceutical composition includes a solution of 3-acyl-buprenorphine, or a pharmaceutically acceptable salt thereof, in a biocompatible organic solvent, wherein the injectable pharmaceutical composition exhibits a steady release profile lasting over one week when injected into a patient. The acyl group is an alkylcarbonyl group, and an alkyl portion of the alkylcarbonyl group is a straight-chain, branched-chain, having 1-20 carbon atoms. The biocompatible organic solvent is N-methyl-2-pyrrolidone, ethyl acetate, ethanol, butanol, 2-butanol, isobutanol, ispropanol, glycerin, benzyl benzoate, dimethyl sulfoxide, N,N-dimethylacetamide, propylene glycol, dimethyl glycol, benzyl alcohol, or a combination of two or more thereof.

7 Claims, 3 Drawing Sheets

SUSTAINED-RELEASE BUPRENORPHINE FORMULATIONS

BACKGROUND OF INVENTION

Field of the Invention

The invention relates generally to a buprenorphine drug delivery system. In particular, the invention relates to an injectable composition comprising buprenorphine, a prodrug, or a metabolite thereof for the treatment of opioid dependence, pain, and depression.

Background Art

Buprenorphine, (5α,7α(s))-17-cyclopropylmethyl)-α-(1,1-dimethylethyl)-4,5-epoxy-18,19-dihydro-3-hydroxy-6-methoxy-α-methyl-6,14-ethenomorphinan-7-methanol, is a derivative of thebaine, which belongs to the family of opioid alkaloids. The structure of buprenorphine is shown as the following formula (Formula I) with a molecular weight of 467.64:

Formula I

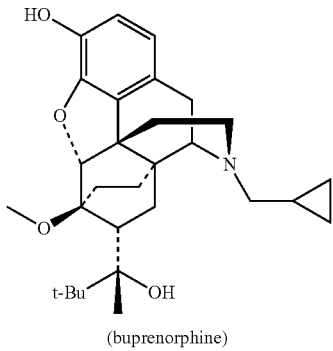

(buprenorphine)

As a partial and potent μ-receptor agonist, buprenorphine has a higher affinity to compete with other full agonists, such as morphine, methadone, etc. With 25~40 times higher potency than that of morphine, buprenorphine is indicated for the treatment of moderate to severe chronic pain, and pre-operative analgesia in several dosage forms, e.g. Buprenex® (intramuscular or intravenous injection), Norspan®, Butrans® (transdermal patch), Temgesic® (sublingual tablet), and Belbuca® (buccal film). The therapeutic concentrations (Cmax) of Butrans in healthy subjects range from 0.1 to 0.5 ng/mL, corresponding to a dose of 5-20 μg/hour. In addition, various products of buprenorphine hydrochloride are approved for treating opioid addiction in higher dosages, e.g. Subutex® (sublingual tablet), and some are combination products of buprenorphine hydrochloride and naloxone hydrochloride e.g. Suboxone® (sublingual film, in 4:1 ratio of buprenorphine hydrochloride and naloxone hydrochloride), Zubsolv® (sublingual tablet), and Bunavail® (buccal film). The therapeutic concentrations (Cmax) of Suboxone range from 1 to 6 ng/mL, corresponding to a dose of 2-16 mg sublingual films. Furthermore, buprenorphine is also a potent antagonist of κ-opioid receptor, and this feature could result in the reduction of tolerance and antidepressant effect. Recently, buprenorphine is utilized to form a combination product, ALK-5461, which consists of buprenorphine (κ-receptor antagonist) and samidorphan (μ-receptor agonist) and has been announced for anti-depressant effect.

In previous studies, various buprenorphine derivatives were disclosed. Among them, modifications of the phenol group by forming ester bond linkages are more common. These ester derivatives are synthesized and compared with buprenorphine and hydrochloride salt thereof. In 1995, Stinchcomb et al. published an article about 3-alkyl ester derivatives of buprenorphine in *Pharm. Res* (1995), 12, 1526-1529 (Formula II, R=acetyl, propanoyl, butanoyl, pentanoyl, hexanoyl, heptanoyl). These derivatives were viewed as prodrugs and purported to improve the physiochemical characteristics of the parent compound to increase the relative permeability through skin in the following articles: *Biol. Pharm. Bull.* (1996), 19, 263-267 and *Pharm. Res.* (1996), 13, 1519-1523.

Formula II

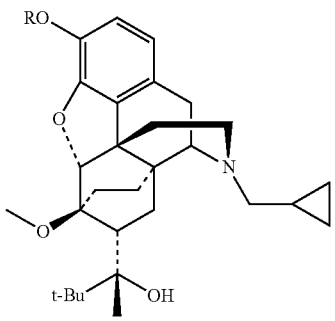

Thereafter, several C3-esterfied buprenorphine derivatives and the applications thereof have been disclosed in various patents. For example, U.S. Pat. No. 7,084,150, issued to Euro-Celtique S. A., describes a huge family of buprenorphine prodrugs and analogs, which include ester bonds or ether bond modified derivatives. EP Patent No. 1422230, issued to Jhi-Joung Wang, discloses dimerized derivatives of buprenorphine and similar alkylcarbonyl derivatives. Prodrug strategy and oil carrier were introduced by an intramuscular or subcutaneous injection, which displays prolong analgesia actions from 5 hours to 96 hours.

A series of buprenorphine ester derivatives also described in U.S. Pat. No. 7,964,610, issued to Reckitt Benckiser Healthcare (UK) Limited. Buprenorphine was modified with dicarboxylic acids or esters. Then, these derivatives were used for the treatment of opiate abuse/dependence and for the treatment of moderate to severe pain.

There are a variety of sustained release designs for buprenorphine indicated for the treatment of opioid dependence and chronic pain. For example, Titan pharmaceuticals, Inc. developed a subcutaneous implant product of buprenorphine hydrochloride, Probuphine®, using their novel drug delivery system, ProNeura™, which is made from a mixture of ethylene vinyl acetate (EVA) and drug substance. Probuphine® is administrated once every six month through surgical implantation and removed from patients after treatment by surgical procedures.

Camurus established a novel technology for drug delivery systems, FluidCrystal®, which is based on lipid liquid crystals that are composed of phosphatidyl choline and glycerol dioleate. The formulation disclosed in US Publication No. 2013/0190341 is designed as a long-acting buprenorphine product to treat opioid dependence and chronic pain, and is administrated by subcutaneous injection weekly or monthly.

U.S. Patent Application Publication No. 2003/0152638, by Brookwood Pharmaceuticals, Inc., discloses an injectable slow-release microsphere formulation that comprises buprenorphine and poly(D,L-lactide). This formulation is able to treat heroin and alcohol abuse for a period of at least 28 days in a mammal.

U.S. Patent Application Publication No. 2014/0271869 (Oakwood Laboratories LLC) disclosed a biodegradable formulation, which utilized their proprietary technology, Chroniject™. The platform is a polymer-based injectable microspheres system for drug delivery. The buprenorphine microspheres could be generated in higher drug load and claimed to achieve sustained release for at least one month to several months.

Indivior PLC (WO 2011/154724) developed a monthly depot, which employed Atrigel system to produce an injectable flowable formulation for the treatment of opioid dependency. The composition includes buprenorphine free base, biodegradable polymer, and a biocompatible solvent. The dissolved liquid could be injected and transformed in situ into a solid implant, providing 1-month and 3-month release profiles. In addition, a suspension and solution designs are disclosed in WO 2011/154725 and WO 2015/136253, respectively. The suspension is composed of buprenorphine and polyethylene glycol polymer in aqueous conditions, providing a therapeutic period of between 7 and 30 days in dogs after a single intramuscular or subcutaneous injection. As for the disclosed solution, the composition consists of buprenorphine or a salt form thereof and a biocompatible organic solvent without a biodegradable polymer. After a single subcutaneous injection in beagle dogs, the formulation is able to provide at least one-month therapeutic period.

According to the description above, these prior art systems are able to perform sustained releases. However, there is still a need to develop a formulation with better characteristics, such as a simpler manufacturing process, an accessible administration procedure, a smoother releasing profile without severe initial burst, or a longer therapeutically effective duration after a single injection.

SUMMARY OF INVENTION

Embodiments of the present invention relate to a sustained-release pharmaceutical composition of buprenorphine, a prodrug or a metabolite thereof, forming a depot in situ for a therapeutically effective duration of at least one week to several months.

One aspect of the invention relates to injectable pharmaceutical compositions. An injectable pharmaceutical composition in accordance with one embodiment of the invention includes a solution of 3-acyl-buprenorphine, or a pharmaceutically acceptable salt thereof, in a biocompatible organic solvent, wherein the injectable pharmaceutical composition exhibits a steady release profile lasting over one week when injected into a patient or an animal.

In accordance with embodiments of the invention, the acyl group is an alkylcarbonyl group or an arylcarbonyl group. An alkyl portion of the alkylcarbonyl group is a straight-chain, branched-chain, having 1-20 carbon atoms. An aryl group in the arylcarbonyl group contains an aromatic ring having 6-18 carbons.

In accordance with embodiments of the invention, the biocompatible organic solvent is N-methyl-2-pyrrolidone, ethyl acetate, ethanol, butanol, 2-butanol, isobutanol, ispropanol, glycerin, benzyl benzoate, dimethyl sulfoxide, N,N-dimethylacetamide, propylene glycol, dimethyl glycol, benzyl alcohol, an ester, an ether, an amide, a carbonate, a lactam, a sulfonyl, or any combination thereof.

In accordance with embodiments of the invention, the 3-acyl buprenorphine, or a pharmaceutically acceptable salt thereof, is present at a concentration of 1-99% w/v, preferably 5-90% w/v, more preferably 10-80% w/v, most preferably 10-60% w/v.

In accordance with embodiments of the invention, an injectable pharmaceutical composition may further comprise a preservative. In accordance with embodiments of the invention, the preservative is selected from the group consisting of methylparaben, propylparaben and benzylalcohol.

In accordance with embodiments of the invention, an injectable pharmaceutical composition is formulated for subcutaneous, intramuscular or intradermal injection.

Another aspect of the invention relates to methods for treating opioid addiction, pain, or depression. A method in accordance with one embodiment of the invention comprises administering to a subject in need thereof a therapeutically effective amount of the injectable pharmaceutical composition according to any embodiment described above.

In accordance with embodiments of the invention, the administering is performed at a frequency of once per week, once per month, preferably once every three months, and more preferably once every six months.

Other aspects of the invention will become apparent with the attached drawings and the following detailed description.

DETAILED DESCRIPTION

Figure 1:
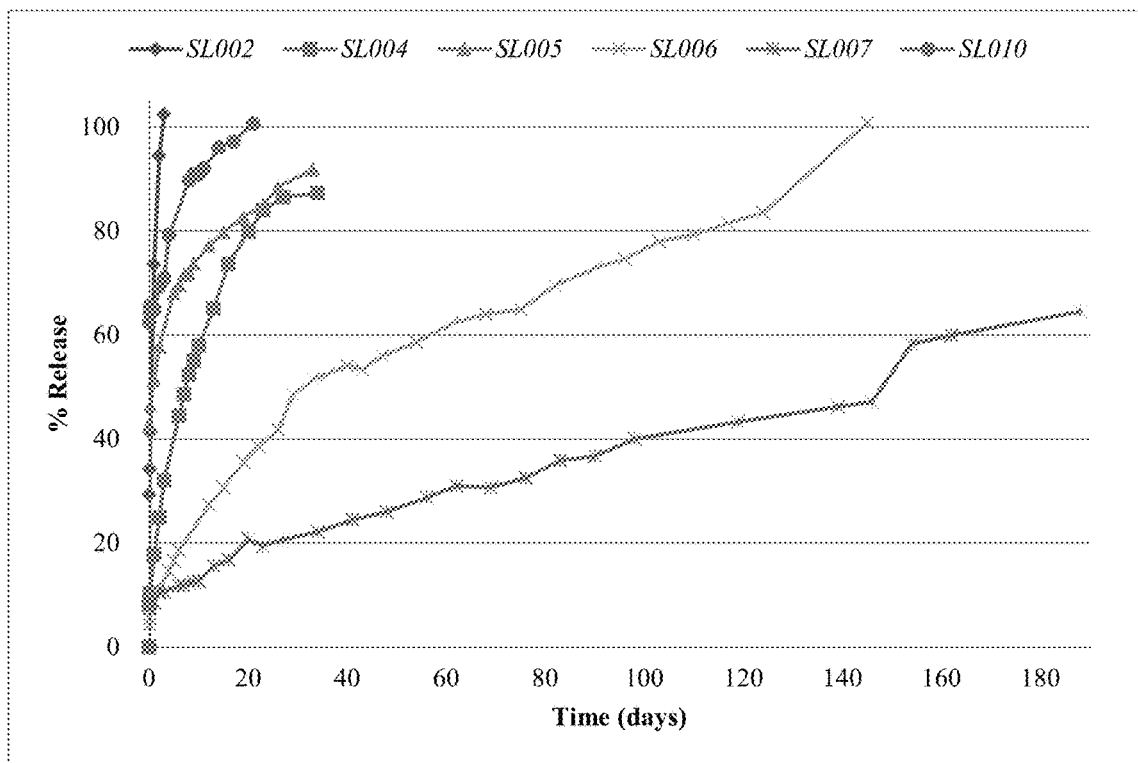
FIG. 1 shows in vitro dissolution profiles of formulations containing various buprenorphine derivatives, in accordance with embodiments of the invention.

Embodiments of the invention relate to formulations of buprenorphine derivatives that exhibit no or minimal initial bursts and have long-lasting release profiles after a single dose administration into a subject in need of treatments. The treatments may include treatments for opioid addiction, pain, or depression. In accordance with embodiments of the invention, the buprenorphine derivatives are 3-alkyl ester derivatives, i.e., esters formed between the 3-hydroxy (phenol) group of buprenorphine and alkylcarbonylation or arylcarbonylation (acylation) reagents.

In accordance with embodiments of the invention, an alkylcarbonyl or arylcarbonyl (i.e., acyl) reagent (R—CO—X), wherein R is an alkyl or aryl residue, may be an acyl chloride, an acyl anhydride, or an acyl active ester. The alkyl portion of an alkylcarbonyl group may be a straight-chain or branched alkyl group. The alkyl portion may contain any suitable number of carbons, such as 1-20 ($C_1$-$C_{20}$), 1-18 ($C_1$-$C_{18}$), 1-16 ($C_1$-$C_{16}$), 1-12 ($C_1$-$C_{12}$), 1-10 ($C_1$-$C_{10}$), 1-5 ($C_1$-$C_5$), or 1-3 ($C_1$-$C_3$). Examples of alkylcarbonyl (acyl) groups may include acetyl, propionyl butyryl, stearyl, and palmityl. The aryl in the arylcarbonyl group is used herein in a broad sense to include not only an aryl group, but also an aryl-alkyl group, wherein the alkyl portion is as defined above. The aryl portion of the arylcarbonyl group may be a $C_6$-$C_{18}$ aromatic ring, such as a phenyl or naphthyl.

In accordance with embodiments of the invention, the buprenorphine derivatives may be synthesized using conventional methods. Buprenorphine or its salt can be purchased from several commercial sources, such as Sigma-Aldrich. To prepare a buprenorphine derivative, buprenorphine (or its salt) may be reacted with an acyl chloride in the presence of a non-nucleophilic base (e.g., triethylamine) to form the ester bond. The product (3-acyl-byprenorphine or 3-alkylcarbonyl-buprenorphine) may be purified with conventional methods (e.g., column chromatography).

As used in this description, a buprenorphine derivative refers to 3-acyl-buprenorphine (3-alkylcarbonyl-buprenorphine or 3-arylcarbonyl-buprenorphine) or a salt thereof. A buprenorphine derivative of the invention may function as a prodrug, which may be converted into the parent compound, buprenorphine.

A formulation of the invention may comprise a buprenorphine derivative dissolved in one or more suitable biocompatible solvents. The buprenorphine derivative may be in the form of a free base or a pharmaceutically acceptable salt thereof, such as a salt of HCL, formate, acetate, or the like. The biocompatible solvents may be organic solvents, such as N-methyl-2-pyrrolidone (NMP), ethyl acetate (EtOAc), ethanol (EtOH), butanol, 2-butanol, isobutanol, glycerin, benzyl benzoate (BnBzO), dimethyl sulfoxide, propylene glycol, dimethyl glycol, and benzyl alcohol.

The formulations of the invention may contain the buprenorphine derivative or a salt thereof in any suitable concentration, such as 1-99% w/v, preferably 1-90% w/v, more preferably 5-90% w/v, more preferably 5-80% w/v, more preferably 10-70% w/v, more preferably 10-60% w/v. Please note that when a numerical range is disclosed in this description, it is intended to include all numbers within the ranges, as if each of these numbers have been individually disclosed.

A formulation of the invention may further comprise another pharmaceutically acceptable excipient, carrier, diluent, or preservative. In accordance with embodiments of the invention, a preservative is preferably selected from the group consisting of methylparaben, propylparaben and benzylalcohol.

Formulations of the invention do not have undesirable initial bursts. However, due to the unique combination of the buprenorphine derivatives and the biocompatible solvents, these formulations can form depots at the administration sites to maintain long-term steady releases of the buprenorphine derivative, buprenorphine, or a metabolite of buprenorphine. Therefore, a formulation of the invention can achieve low or no initial burst (avoiding the undesirable adverse effects) and yet can maintain therapeutically effective levels of buprenorphine over a long duration. A long duration (or a steady release profile) in accordance with embodiments of the invention may last over 1 week, preferably over 2 weeks, more preferably over 1 month, and most preferably over 2 months (e.g., 3 months, 4 months, 5 months, 6 months, or longer).

Because these formulations do not have appreciable initial bursts, they can be given at higher doses, such as up to 800 mg/Kg body weight, preferable 120 mg/Kg, more preferably 60 mg/Kg, most preferably 40 mg/kg. A therapeutically effective dose is a dose that will achieve the intended therapeutic effects. One skilled in the art would appreciate that a therapeutically effective dose would depend on many factors, such as patient conditions, age, sex, weight, route of administration, etc. One skilled in the art would be able to determine a therapeutically effective dose without inventive efforts.

Due to the unique combination of buprenorphine derivatives and the biocompatible solvents, the formulations of the invention have the advantages that less frequent injections are required and patient compliance would be improved.

Embodiments of the invention will be further illustrated with the following specific examples. However, one skilled in the art would appreciate that these examples are for illustration only and that other modifications and variations are possible without departing from the scope of the invention.

Example 1—Preparation of Buprenorphine Derivatives

The buprenorphine derivatives were synthesized using typical methods outlined in the following description. To a 3-necked round-bottom flask, buprenorphine HCl and dichloromethane were added to form a suspension, which was then placed in an ice bath for cooling. After that, triethylamine was added slowly with stirring. Acyl chloride was then added dropwise into the flask. Any suitable acyl chloride of a fatty acid may be used, such as $C_1$-$C_{20}$ acyl chloride, preferably $C_2$-$C_{18}$ acyl chloride, more preferably $C_2$-$C_{12}$ acyl chloride. Removed the ice bath, the esterified reaction was carried out under nitrogen atmosphere at ambient temperature. The reaction mixture was neutralized with saturated sodium bicarbonate aqueous solution. The organic layer was washed with brine and then dried with sodium sulfate. After concentration under reduced pressure, the crude buprenorphine derivative was purified with silica gel column chromatography.

Example 2—Preparation of Formulations

Buprenorphine derivative (10 wt %-60 wt %) was added into a glass vial and dissolved with one or a combination of two or more biocompatible organic solvent (e.g. N-methyl-2-pyrrolidone (NMP), ethyl acetate (EtOAc), ethanol (EtOH), butanol, 2-butanol, isobutanol, glycerin, benzyl benzoate (BnBzO), dimethyl sulfoxide, N,N-dimethylacetamide, propylene glycol, dimethyl glycol, benzyl alcohol). The mixture was stirred constantly at ambient temperature or heated slightly until all the ingredients were dissolved. Exemplary formulation compositions are listed in Table 1.

TABLE 1

| Formulation | API, wt % | Solvent 1, wt % | Solvent 2, wt % |
|---|---|---|---|
| SL001 | Buprenorphine free base, 30% | NMP, 70% | — |
| SL002 | Buprenorphine acetate, 30% | NMP, 70% | — |
| SL003 | Buprenorphine pentanoate, 30% | NMP, 70% | — |
| SL004 | Buprenorphine hexanoate, 30% | NMP, 70% | — |
| SL005 | Buprenorphine pivalate, 30% | NMP, 70% | — |
| SL006 | Buprenorphine decanoate, 30% | NMP, 70% | — |
| SL007 | Buprenorphine dodecanoate, 30% | NMP, 70% | — |
| SL008 | Buprenorphine palmitate, 30% | NMP, 70% | — |
| SL009 | Buprenorphine stearate, 30% | NMP, 70% | — |
| SL010 | Buprenorphine benzonate, 15% | NMP, 85% | — |
| SL011 | Buprenorphine decanoate, 15% | NMP, 85% | — |
| SL012 | Buprenorphine decanoate, 20% | NMP, 80% | — |
| SL013 | Buprenorphine decanoate, 25% | NMP, 75% | — |
| SL014 | Buprenorphine decanoate, 30% | EtOAc, 40% | EtOH, 30% |
| SL015 | Buprenorphine decanoate, 50% | EtOAc, 50% | — |
| SL016 | Buprenorphine decanoate, 45% | EtOAc, 55% | — |
| SL017 | Buprenorphine decanoate, 50% | EtOAc, 40% | EtOH, 10% |
| SL018 | Buprenorphine decanoate, 50% | EtOAc, 45% | EtOH, 5% |
| SL019 | Buprenorphine decanoate, 35% | EtOAc, 58.5% | EtOH, 6.5% |
| SL020 | Buprenorphine decanoate, 35% | EtOAc, 52% | EtOH, 13% |
| SL021 | Buprenorphine decanoate, 40% | EtOAc, 54% | EtOH, 6% |
| SL022 | Buprenorphine decanoate, 40% | EtOAc, 48% | EtOH, 12% |
| SL023 | Buprenorphine decanoate, 45% | EtOAc, 49.5% | EtOH, 5.5% |
| SL024 | Buprenorphine decanoate, 45% | EtOAc, 44% | EtOH, 11% |
| SL025 | Buprenorphine decanoate, 40% | BnBzO, 60% | — |
| SL026 | Buprenorphine decanoate, 80% | BnBzO, 20% | — |
| SL027 | Buprenorphine decanoate, 90% | BnBzO, 10% | — |
| SL028 | Buprenorphine hexanoate, 50% | NMP, 50% | — |
| SL029 | Buprenorphine hexanoate, 50% | EtOAc, 50% | — |
| SL030 | Buprenorphine hexanoate, 50% | EtOAc, 45% | EtOH, 5% |
| SL031 | Buprenorphine hexanoate, 50% | EtOAc, 40% | EtOH, 10% |
| SL032 | Buprenorphine dodecanoate, 50% | EtOAc, 50% | — |
| SL033 | Buprenorphine dodecanoate, 50% | EtOAc, 63% | EtOH, 7% |
| SL034 | Buprenorphine dodecanoate, 30% | EtOAc, 56% | EtOH, 14% |
| SL035 | Buprenorphine dodecanoate, 35% | NMP, 65% | — |

Example 3—In Vitro Dissolution Test of the Formulations

Figure 2:
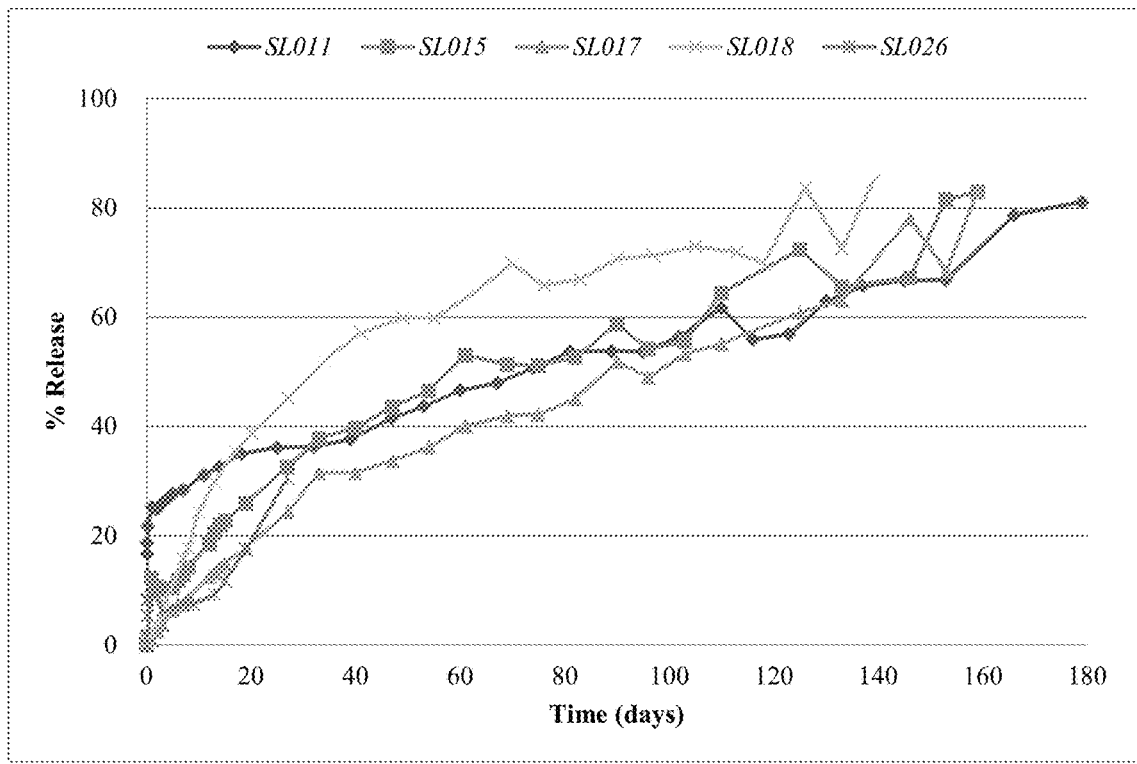
FIG. 2 shows in vitro dissolution profiles of formulations containing buprenorphine decanoate in various weight ratio and solvents combinations, in accordance with embodiments of the invention.
Figure 3:
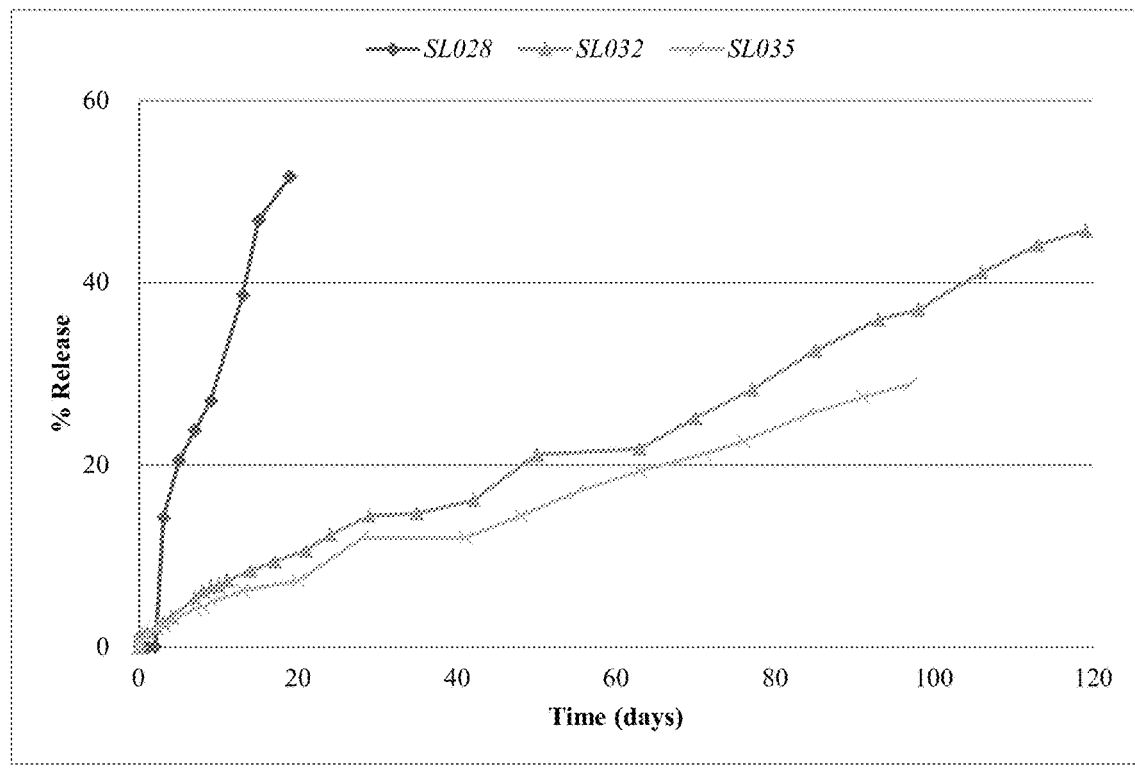
FIG. 3 shows in vitro dissolution profiles of formulations containing buprenorphine hexanoate and dodecanoate in various solvents, in accordance with embodiments of the invention.

The formulations in example 2 were assessed for their in vitro dissolution profiles. The dissolution medium comprises 1% sodium dodecyl sulfate and 0.02% sodium azide in phosphate buffered saline. The dissolution medium for formulation SL028 and S032 comprise 0.2% sodium dodecyl sulfate and 0.02% sodium azide in phosphate buffered saline. The tubes were incubated in a reciprocal shaker at the rate of 60 rpm in a 55° C. water bath. The tubes were pulled, samples of 1 mL solution were removed, and the tubes were refilled with 1 mL fresh medium at specified times. The removed samples were analyzed with HPLC for buprenorphine derivatives and their parent compound, buprenorphine free base. The dissolution profiles are shown in FIG. 1-3 and Table 2-4.

TABLE 2

| Time (days) | % Release | | | | | |
|---|---|---|---|---|---|---|
| | SL002 | SL005 | SL004 | SL006 | SL007 | SL010 |
| 0 | 0.0 | 0.0 | 0.0 | 0.0 | 0.0 | 0.0 |
| 0.042 | 29.4 | 42.9 | 8.2 | 4.3 | 7.4 | 62.4 |
| 0.083 | 34.3 | 42.9 | 9.0 | 5.6 | 7.6 | 64.4 |
| 0.167 | 41.4 | 46.3 | 10.3 | 7.6 | 8.8 | 65.6 |
| 1 | 73.6 | 51.3 | 17.7 | 8.9 | 8.6 | 64.9 |
| 2 | 94.4 | 57.8 | 24.9 | 10.5 | 10.7 | 69.3 |
| 3 | 102.4 | — | 32.0 | 12.9 | 10.7 | — |
| 4 | — | — | — | 14.7 | — | — |
| 5 | — | 68.1 | — | 16.6 | — | 71.0 |
| 6 | — | 69.7 | 44.5 | 18.6 | 11.9 | 79.2 |
| 7 | — | 71.6 | 48.6 | 20.0 | 11.8 | 89.7 |
| 8 | — | 72.0 | 52.4 | — | 12.2 | 90.9 |
| 9 | — | 73.8 | 55.1 | — | 12.4 | 90.8 |
| 10 | — | — | 57.9 | — | 12.7 | — |
| 12 | — | 77.2 | — | 27.3 | — | 92.0 |
| 13 | — | — | 65.1 | — | 15.6 | — |
| 15 | — | 79.7 | — | 30.7 | — | 96.0 |
| 16 | — | — | 73.7 | — | 16.7 | — |
| 19 | — | 82.5 | — | 35.6 | — | 97.2 |
| 20 | — | — | 79.8 | — | 20.8 | — |
| 22 | — | — | — | 38.6 | — | — |
| 23 | — | 84.9 | 84.1 | — | 19.5 | 100.6 |
| 26 | — | 88.4 | — | 41.8 | — | — |
| 27 | — | — | 86.5 | — | 20.6 | — |
| 29 | — | — | — | 48.4 | — | — |
| 33 | — | 91.8 | — | 51.5 | — | — |
| 34 | — | — | 87.3 | — | 22.1 | — |
| 36 | — | — | — | 52.5 | — | — |
| 40 | — | — | — | 54.1 | — | — |
| 41 | — | — | 86.8 | — | 24.5 | — |
| 43 | — | — | — | 53.4 | — | — |
| 47 | — | — | — | 56.0 | — | — |
| 48 | — | — | 86.4 | — | 26.0 | — |
| 54 | — | — | — | 58.6 | — | — |
| 56 | — | — | 81.9 | — | 28.7 | — |
| 61 | — | — | — | 62.1 | — | — |
| 62 | — | — | — | — | 31.0 | — |
| 68 | — | — | — | 64.1 | — | — |
| 69 | — | — | — | — | 30.7 | — |
| 75 | — | — | — | 64.9 | — | — |
| 76 | — | — | — | — | 32.5 | — |
| 82 | — | — | — | 69.6 | — | — |
| 83 | — | — | — | — | 35.9 | — |
| 90 | — | — | — | 72.9 | 36.7 | — |
| 96 | — | — | — | 74.6 | — | — |
| 98 | — | — | — | — | 40.0 | — |
| 103 | — | — | — | 78.0 | — | — |
| 110 | — | — | — | 79.3 | — | — |
| 117 | — | — | — | 81.5 | — | — |
| 119 | — | — | — | — | 43.3 | — |
| 124 | — | — | — | 83.5 | — | — |
| 131 | — | — | — | — | — | — |
| 139 | — | — | — | — | 46.2 | — |
| 145 | — | — | — | 100.8 | — | — |
| 146 | — | — | — | — | 47.2 | — |
| 152 | — | — | — | — | — | — |
| 154 | — | — | — | — | 58.3 | — |
| 162 | — | — | — | — | 59.9 | — |
| 188 | — | — | — | — | 64.5 | — |

TABLE 3

| Time (days) | % Release | | | | |
|---|---|---|---|---|---|
| | SL011 | SL015 | SL017 | SL018 | SL026 |
| 0 | 0.0 | 0.0 | 0.0 | 0.0 | 0.0 |
| 0.042 | 16.6 | 0.4 | 0.3 | 0.7 | 8.2 |
| 0.083 | 18.8 | 0.2 | 0.1 | 0.6 | 8.3 |
| 0.167 | 21.8 | 1.6 | 0.2 | 0.7 | 5.4 |
| 1 | 25.2 | 12.3 | 0.9 | 2.2 | 8.7 |
| 2 | 24.8 | 10.7 | 2.5 | 4.2 | 9.1 |
| 3 | 26.0 | 10.2 | 3.7 | 6.5 | 6.0 |
| 4 | 26.7 | — | — | — | — |
| 5 | 28.3 | 10.5 | 6.3 | — | 6.9 |
| 6 | — | 11.8 | 7.3 | — | — |
| 7 | 28.3 | 12.8 | 7.5 | 15.8 | 7.5 |
| 8 | — | 14.3 | 8.7 | 17.9 | — |
| 9 | — | — | — | — | 7.4 |
| 10 | — | — | — | 24.4 | — |
| 11 | 31.2 | — | — | — | — |

TABLE 3-continued

| | % Release | | | | |
|---|---|---|---|---|---|
| Time (days) | SL011 | SL015 | SL017 | SL018 | SL026 |
| 12 | — | 18.5 | 12.5 | — | — |
| 13 | — | 20.6 | 13.3 | 29.9 | 9.3 |
| 14 | 32.6 | 21.9 | 14.3 | — | — |
| 15 | — | 22.8 | 14.9 | — | 11.7 |
| 17 | — | — | — | 35.5 | — |
| 18 | 35.0 | — | — | — | — |
| 19 | — | 25.9 | 17.7 | — | 17.5 |
| 20 | — | — | — | 38.8 | — |
| 25 | 36.2 | — | — | — | — |
| 27 | — | 32.6 | 24.4 | 45.2 | 30.6 |
| 32 | 36.3 | — | — | — | — |
| 33 | — | 37.8 | 31.6 | — | — |
| 34 | — | — | — | 52.1 | — |
| 39 | 37.6 | — | — | — | — |
| 40 | — | 39.8 | 31.6 | — | — |
| 41 | — | — | — | 57.1 | — |
| 42 | — | — | — | — | — |
| 47 | 41.5 | 43.6 | 33.8 | — | — |
| 49 | — | — | — | 59.9 | — |
| 53 | 43.7 | — | — | — | — |
| 54 | — | 46.6 | 36.2 | — | — |
| 55 | — | — | — | 59.8 | — |
| 60 | 46.6 | — | — | — | — |
| 61 | — | 53.1 | 40.0 | — | — |
| 62 | — | — | — | 64.0 | — |
| 67 | 48.0 | — | — | — | — |
| 69 | — | 51.4 | 42.0 | — | — |
| 70 | — | — | — | 69.7 | — |
| 74 | 50.6 | — | — | — | — |
| 76 | — | — | — | 65.8 | — |
| 81 | 53.7 | — | — | — | — |
| 82 | — | 52.6 | 45.1 | — | — |
| 83 | — | — | — | 67.0 | — |
| 89 | 53.8 | — | — | — | — |
| 90 | — | 58.8 | 51.9 | 70.7 | — |
| 95 | 53.7 | — | — | — | — |
| 96 | — | 54.2 | 49.0 | — | — |
| 97 | — | — | — | 71.3 | — |
| 102 | 56.4 | — | — | — | — |
| 103 | — | 55.5 | 53.2 | — | — |
| 105 | — | — | — | 73.0 | — |
| 110 | 61.8 | 64.4 | 55.1 | — | — |
| 113 | — | — | — | 71.9 | — |
| 116 | 55.9 | — | — | — | — |
| 118 | — | — | — | 69.8 | — |
| 123 | 56.9 | — | — | — | — |
| 125 | — | 72.5 | 60.9 | — | — |
| 126 | — | — | — | 83.7 | — |
| 130 | 62.9 | — | — | — | — |
| 133 | — | 65.6 | 63.1 | 72.6 | — |
| 137 | 65.6 | — | — | — | — |
| 138 | — | 62.9 | 60.9 | — | — |
| 139 | — | — | — | 84.9 | — |
| 145 | 66.7 | — | — | — | — |
| 146 | — | 67.2 | 78.1 | — | — |
| 153 | 66.8 | 81.6 | 68.4 | — | — |
| 158 | 63.4 | — | — | — | — |
| 159 | — | 82.9 | 83.1 | — | — |
| 166 | 78.7 | — | — | — | — |
| 173 | 67.4 | — | — | — | — |
| 179 | 81.1 | — | — | — | — |

TABLE 4

| | % Release | | |
|---|---|---|---|
| Time (days) | SL028 | SL032 | SL035 |
| 0 | 0.0 | 0.0 | 0.0 |
| 0.042 | 0.0 | 1.3 | 0.6 |
| 0.083 | 0.0 | 1.3 | 0.6 |
| 0.167 | 0.0 | — | — |
| 1 | 0.0 | 1.7 | 1.5 |

TABLE 4-continued

| | % Release | | |
|---|---|---|---|
| Time (days) | SL028 | SL032 | SL035 |
| 2 | 0.0 | 2.1 | 2.0 |
| 3 | 14.1 | 2.8 | 2.4 |
| 4 | — | 3.3 | — |
| 5 | 20.5 | — | — |
| 7 | 23.8 | 5.4 | 4.2 |
| 8 | — | 6.2 | 4.5 |
| 9 | 27.1 | 6.6 | 4.9 |
| 10 | — | 6.8 | 5.2 |
| 11 | — | 7.3 | — |
| 13 | 38.6 | — | 6.2 |
| 14 | — | 8.4 | — |
| 15 | 46.9 | — | — |
| 17 | — | 9.3 | — |
| 19 | 51.7 | — | — |
| 20 | — | — | 7.2 |
| 21 | — | 10.5 | — |
| 24 | — | 12.3 | — |
| 27 | — | — | — |
| 28 | — | — | 11.9 |
| 29 | — | 14.4 | — |
| 34 | — | — | — |
| 35 | — | 14.7 | — |
| 41 | — | — | 12.0 |
| 42 | — | 16.1 | — |
| 48 | — | — | 14.4 |
| 49 | — | — | — |
| 50 | — | 21.1 | — |
| 55 | — | — | 17.0 |
| 63 | — | 21.8 | 19.3 |
| 70 | — | 25.1 | — |
| 71 | — | — | 21.2 |
| 76 | — | — | 22.6 |
| 77 | — | 28.3 | — |
| 84 | — | — | 25.5 |
| 85 | — | 32.6 | — |
| 91 | — | — | 27.5 |
| 93 | — | 36.0 | — |
| 97 | — | — | 28.9 |
| 98 | — | 37.1 | — |
| 106 | — | 41.1 | — |
| 113 | — | 44.1 | — |
| 119 | — | 45.7 | — |

Example 4—Pharmacokinetic Profiles of the Formulations in Rats

The formulations from Example 2 were injected subcutaneously into CD (SD) IGS male rats at a dose of 30-90 mg buprenorphine/kg. Blood samples were collected from tail veins at specific time points. Plasma samples were separated by centrifuge and stored in frozen conditions for later analysis. LC-MS/MS was used to analyze the concentrations of buprenorphine in the plasma samples. The results are shown in Table 5-7 and FIG. 4-6.

TABLE 5

| | SL006 | | | | | |
|---|---|---|---|---|---|---|
| Time | 30 mg/kg | | 60 mg/kg | | 90 mg/kg | |
| (days) | Mean (ng/mL) | S.D.(n = 3) | Mean (ng/mL) | S.D.(n = 3) | Mean (ng/mL) | S.D.(n = 3) |
| pre | 0.00 | 0.00 | 0.00 | 0.00 | 0.00 | 0.00 |
| 0.021 | 0.00 | 0.00 | 3.06 | 1.61 | 0.35 | 0.44 |
| 0.042 | 0.17 | 0.15 | 4.78 | 2.16 | 1.38 | 1.13 |
| 0.083 | 0.73 | 0.42 | 3.35 | 2.22 | 2.29 | 0.79 |
| 0.17 | 1.32 | 0.63 | 3.71 | 2.03 | 3.93 | 0.42 |
| 0.25 | 1.66 | 0.49 | 3.25 | 1.47 | 4.42 | 0.74 |
| 1 | 0.93 | 0.21 | 3.11 | 0.60 | 3.38 | 0.45 |
| 3 | 0.55 | 0.24 | 1.96 | 0.22 | 3.24 | 0.9 |
| 7 | 0.85 | 0.14 | 2.5 | 0.88 | 3.92 | 0.71 |
| 10 | 1.06 | 0.6 | 3.7 | 0.99 | 6.23 | 0.82 |
| 14 | 0.74 | 0.22 | 5.55 | 3.67 | 6.43 | 0.29 |
| 21 | 1.34 | 0.56 | 4.87 | 3.16 | 8.79 | 1.86 |
| 28 | 0.58 | 0.41 | 2.05 | 0.93 | 6.07 | 1.05 |
| 35 | 0.25 | 0.29 | 6.43 | 4.57 | 5.39 | 1.31 |
| 42 | 0.18 | 0.28 | 2.67 | 0.67 | 4.21 | 0.65 |
| 49 | — | — | 1.96 | 0.65 | 5.39 | 0.24 |
| 56 | — | — | 1.92 | 0.48 | 4.08 | 0.13 |
| 63 | — | — | 1.75 | 0.28 | 4.51 | 0.48 |
| 70 | — | — | 1.73 | 0.48 | 4.16 | 0.50 |
| 77 | — | — | 1.40 | 0.65 | 4.02 | 0.35 |
| 84 | — | — | 0.72 | 0.16 | 3.61 | 0.46 |
| 91 | — | — | 1.25 | 0.76 | 3.36 | 0.22 |
| 98 | — | — | 0.62 | 0.57 | 3.01 | 0.25 |
| 105 | — | — | 1.09 | 0.05 | 3.05 | 1.21 |
| 112 | — | — | 1.06 | 0.19 | — | — |
| 119 | — | — | 1.06 | 0.15 | — | — |
| 126 | — | — | 0.91 | 0.14 | — | — |
| 133 | — | — | 0.86 | 0.06 | — | — |

TABLE 6

| | SL031 (60 mg/kg) | |
|---|---|---|
| Time (days) | Mean (ng/mL) | S.D.(n = 3) |
| 0 | 0.95 | 1.9 |
| 0.042 | 6.5 | 4.87 |
| 0.083 | 14.7 | 8.3 |
| 0.25 | 28.08 | 21.56 |
| 1 | 13.5 | 5.31 |
| 3 | 16.5 | 6.03 |
| 7 | 20.5 | 7.48 |
| 10 | 16.43 | 5.34 |
| 14 | 11.59 | 3.52 |
| 21 | 8.02 | 3.44 |
| 28 | 5.12 | 2.54 |
| 35 | 4.38 | 2.02 |
| 42 | 3.7 | 2.43 |
| 49 | 2.41 | 1.37 |
| 56 | 2.84 | 1.78 |
| 63 | 4.11 | 1.97 |
| 70 | 3.85 | 1.94 |
| 77 | 2.98 | 1.42 |
| 84 | 2.09 | 1.43 |

TABLE 7

| | SL035 (60 mg/kg) | |
|---|---|---|
| Time (days) | Mean (ng/mL) | S.D.(n = 3) |
| 0 | 0 | 0 |
| 0.042 | 0.23 | 0.25 |
| 0.083 | 0.39 | 0.43 |
| 0.25 | 1.12 | 0.79 |
| 1 | 1.18 | 0.82 |
| 3 | 1.06 | 0.78 |
| 7 | 3.81 | 1.55 |
| 10 | 4.64 | 1.77 |
| 14 | 5.93 | 3.11 |
| 17 | — | — |
| 21 | 4.42 | 2.28 |
| 24 | — | — |
| 28 | 3.50 | 1.45 |
| 35 | 3.18 | 1.29 |
| 42 | 2.37 | 0.94 |
| 49 | 2.18 | 0.89 |
| 56 | 1.91 | 0.78 |
| 63 | 1.88 | 0.70 |
| 70 | 1.59 | 0.38 |
| 77 | 1.45 | 0.38 |
| 84 | 1.45 | 0.46 |
| 98 | 1.21 | 0.34 |
| 115 | 0.91 | 0.06 |
| 126 | 0.85 | 0.13 |
| 140 | 0.97 | 0.23 |
| 154 | 0.73 | 0.17 |
| 168 | 1.04 | 0.18 |

Figure 4:
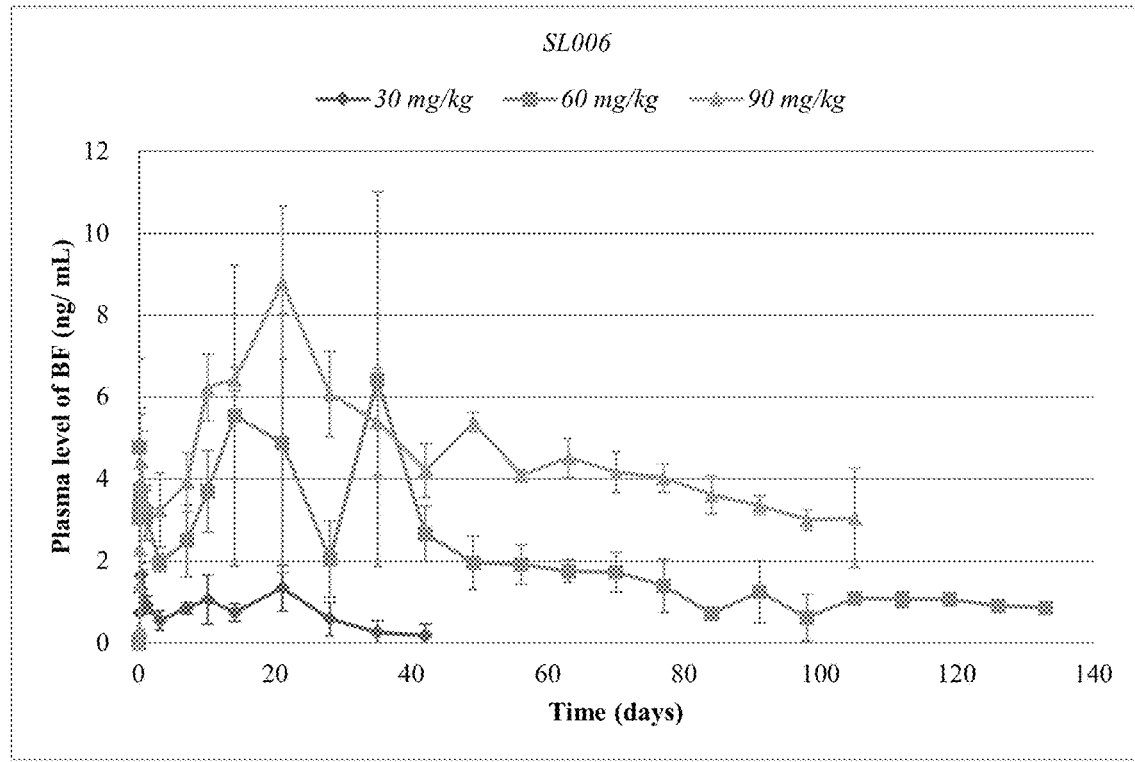
FIG. 4 shows mean plasma levels of buprenorphine after subcutaneous injection of SL006 at the dose of 30, 60, and 90 mg buprenorphine/kg in rats, in accordance with embodiments of the invention.
Figure 5:
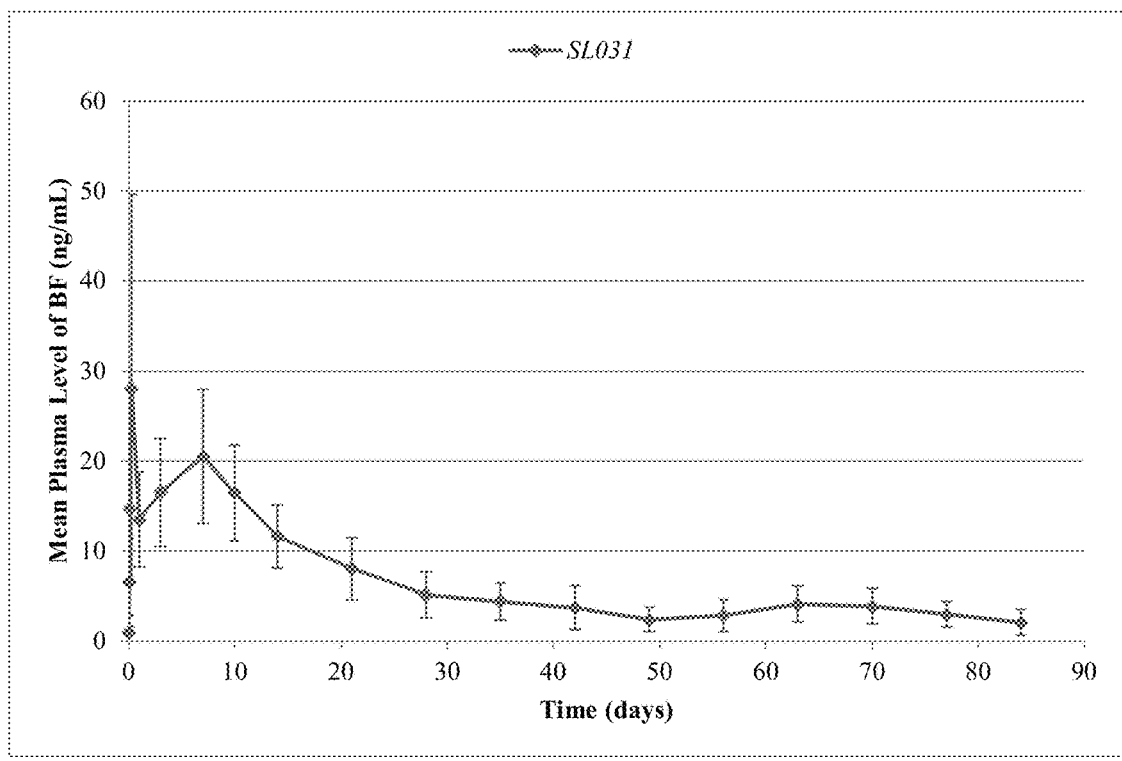
FIG. 5 shows mean plasma levels of buprenorphine after subcutaneous injection of SL031 at the dose of 60 mg buprenorphine/kg in rats, in accordance with embodiments of the invention.
Figure 6:
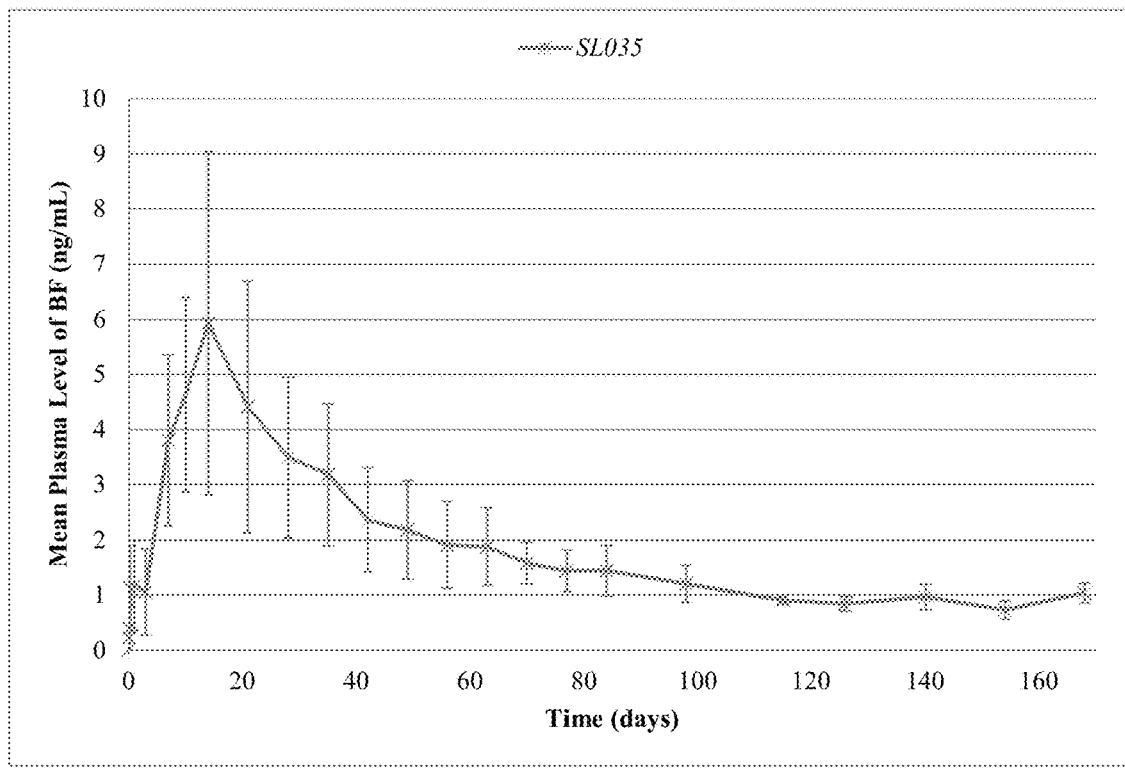
FIG. 6 shows mean plasma levels of buprenorphine after subcutaneous injection of SL035 at the dose of 60 mg buprenorphine/kg in rats, in accordance with embodiments of the invention.

Surprisingly, the formulations of present invention using prodrug strategy and in situ depot formation display zero-order-release curves without initial bursts, See FIGS. 4-6. Conversely, the prior art formulations typically exhibit significant initial bursts, followed by gradually decreasing drug release/uptakes. The initial bursts limit the highest doses that can be used in a single administration; otherwise, adverse effects may occur due to the unacceptable high dose during the initial burst phase.

In contrast, without the initial bursts, formulations of the invention may be given at a higher dose in a single administration without inducing the adverse effects. A higher dose in each administration would allow a single dose to last longer, which is desirable for slow-release formulations.

Furthermore, the zero-order release profiles of the formulations of the invention guarantees that an effective dose will be released over a long duration, expanding the therapeutically effective durations to several months. These highly desirable properties of the formations of the present invention may be due to the use of prodrugs (C3-acyl-buprenorphines, i.e., acyl esters formation with the phenol of buprenorphine) as well as the formulations for the depot formation in situ.

While the invention has been described with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

What is claimed is:

1. An injectable pharmaceutical composition, comprising:
a solution of 3-acyl-buprenorphine, or a pharmaceutically acceptable salt thereof, in a biocompatible organic solvent, wherein the injectable pharmaceutical composition exhibits a steady release profile lasting over one week when injected into a patient or an animal,
wherein the acyl group comprises an alkylcarbonyl group, and wherein the alkyl portion of the alkylcarbonyl group is a straight-chain or branched-chain, having 5-12 carbon atoms,
wherein the biocompatible organic solvent is N-methyl-2-pyrrolidone; and
wherein the 3-acyl buprenorphine, or the pharmaceutically acceptable salt thereof, is present at a concentration of 30% to 60% w/v.

2. The injectable pharmaceutical composition according to claim 1, wherein the acyl group comprises an arylcarbonyl group, wherein an aryl portion of the arylcarbonyl group is an aromatic group having 6-18 carbons.

3. The injectable pharmaceutical composition according to claim 1, further comprising a preservative selected from the group consisting of methylparaben, propylparaben and benzylalcohol.

4. The injectable pharmaceutical composition according to claim 1, wherein the injectable pharmaceutical composition is formulated for subcutaneous, intramuscular or intradermal injection.

5. A method for treating opioid addiction, pain, or depression, comprising administering to a subject in need thereof a therapeutically effective amount of the injectable pharmaceutical composition according to claim 1.

6. The method according to claim 5, wherein the administering is once every week or once every two weeks.

7. The method according to claim 5, wherein the administering is once every month, once every three months, or once every six months.

* * * * *